(12) United States Patent
Mansour et al.

(10) Patent No.: US 11,253,689 B2
(45) Date of Patent: *Feb. 22, 2022

(54) CLOSED MALE LUER DEVICE FOR USE WITH NEEDLELESS ACCESS DEVICES

(71) Applicant: CareFusion 303, Inc., San Diego, CA (US)

(72) Inventors: George Michel Mansour, Diamond Bar, CA (US); Matthew Paul Fried, Milwaukee, WI (US)

(73) Assignee: CareFusion 303, Inc., San Diego, CA (US)

( * ) Notice: Subject to any disclaimer, the term of this patent is extended or adjusted under 35 U.S.C. 154(b) by 342 days.

This patent is subject to a terminal disclaimer.

(21) Appl. No.: 16/457,508

(22) Filed: Jun. 28, 2019

(65) Prior Publication Data
US 2019/0321619 A1  Oct. 24, 2019

Related U.S. Application Data

(63) Continuation of application No. 15/478,157, filed on Apr. 3, 2017, now Pat. No. 10,369,350, which is a
(Continued)

(51) Int. Cl.
*A61M 39/26* (2006.01)
*A61M 39/10* (2006.01)

(52) U.S. Cl.
CPC .......... *A61M 39/26* (2013.01); *A61M 39/10* (2013.01); *A61M 39/1011* (2013.01);
(Continued)

(58) Field of Classification Search
CPC ...... A61M 2039/261; A61M 2039/266; A61M 2039/267; A61M 2039/268; A61M 39/10; A61M 39/1011; A61M 39/26
See application file for complete search history.

(56) References Cited

U.S. PATENT DOCUMENTS 4,969,879 A   11/1990 Lichte
5,569,235 A   10/1996 Ross et al.
(Continued)

FOREIGN PATENT DOCUMENTS

CN   101389372   3/2009
EP   1848913     3/2009
(Continued)

OTHER PUBLICATIONS

European Office Action for Application No. 10762014.8, dated Mar. 22, 2021, 8 pages.
(Continued)

*Primary Examiner* — Brandy S Lee
(74) *Attorney, Agent, or Firm* — Morgan, Lewis & Bockius LLP

(57) ABSTRACT

A medical connector is described which is formed by a body having an inlet port, an outlet port through a male luer portion of the body, and a fluid path between the inlet port and the at least one outlet ports. A retractable post extends through the fluid path in the male luer sealing a tip of the male luer thereby closing the fluid path when the connector in not activated. There is a seal between the retractable post and the body that forms a fluid volume within a portion of the cavity. The fluid path passes through the fluid volume. When actuated, the retractable post is forced away from the tip of the male luer, thereby opening the fluid path through the medical connector and decreasing the fluid volume.

20 Claims, 12 Drawing Sheets

Related U.S. Application Data continuation of application No. 14/172,756, filed on Feb. 4, 2014, now Pat. No. 9,629,994, which is a continuation of application No. 13/455,090, filed on Apr. 24, 2012, now Pat. No. 8,641,685, which is a continuation of application No. 12/418,809, filed on Apr. 6, 2009, now Pat. No. 8,182,452.

(52) U.S. Cl.
CPC . *A61M 2039/261* (2013.01); *A61M 2039/266* (2013.01); *A61M 2039/267* (2013.01); *A61M 2039/268* (2013.01); *Y10T 29/49826* (2015.01)

(56) References Cited

U.S. PATENT DOCUMENTS

| | | | |
|---|---|---|---|
| 7,195,616 | B2 | 3/2007 | Diller et al. |
| 7,329,249 | B2 | 2/2008 | Bonaldo |
| 8,182,452 | B2 * | 5/2012 | Mansour ............ A61M 39/1011 604/256 |
| 8,641,685 | B2 | 2/2014 | Mansour et al. |
| 2001/0049508 | A1 | 12/2001 | Fangrow, Jr. |
| 2003/0032940 | A1 | 2/2003 | Doyle |
| 2003/0060804 | A1 | 3/2003 | Vaillancourt |
| 2004/0124389 | A1 | 7/2004 | Phillips |
| 2004/0171993 | A1 | 9/2004 | Bonaldo |
| 2005/0228362 | A1 | 10/2005 | Vaillancourt |
| 2006/0192164 | A1 | 8/2006 | Korogi |
| 2007/0017583 | A1 | 1/2007 | Fangrow |
| 2007/0083162 | A1 | 4/2007 | O'Reagan et al. |
| 2007/0088292 | A1 | 4/2007 | Fangrow |
| 2007/0088293 | A1 | 4/2007 | Fangrow |
| 2007/0088294 | A1 | 4/2007 | Fangrow |
| 2007/0088324 | A1 | 4/2007 | Fangrow |
| 2007/0088325 | A1 * | 4/2007 | Fangrow, Jr. ......... A61M 39/26 604/533 |
| 2007/0106244 | A1 | 5/2007 | Mosler et al. |

FOREIGN PATENT DOCUMENTS

| | | |
|---|---|---|
| JP | 2009500112 | 1/2009 |
| WO | WO-2005107847 | 11/2005 |
| WO | WO-2006062912 | 6/2006 |
| WO | WO-2007008511 | 1/2007 |

OTHER PUBLICATIONS

Brazil Office Action for Application No. PI1010311-2, dated Dec. 27, 2019, 7 pages.
Australian Office Action for Application No. 2020220186, dated Nov. 9, 2020, 4 pages.
Brazilian Office Action for Application No. BR122020007742-5, dated Oct. 21, 2020, 7 pages including English translation of relevant parts.
India Hearing Notice in Reference of Application No. 7069/CHENP/2011, dated Jan. 8, 2021, 2 pages.
Australian Examination Report No. 1 for Application No. 2018201181, dated Jul. 30, 2018, 4 pages.
Brazilian Office Action for Application No. PI1010311-2, dated Jul. 19, 2019, 7 pages.
Extended European Search Report for Application No. 10762014.8, dated Sep. 6, 2017, 10 pages.
India Office Action for Application No. 7069/CHENP/2011, dated Aug. 27, 2018, 5 pages.
Korean Office Action for Application No. 10-2017-7002221, dated May 12, 2017, 4 pages excluding translation.
Australian Office Action for Application No. 2019204299, dated Dec. 4, 2019, 3 pages.

\* cited by examiner

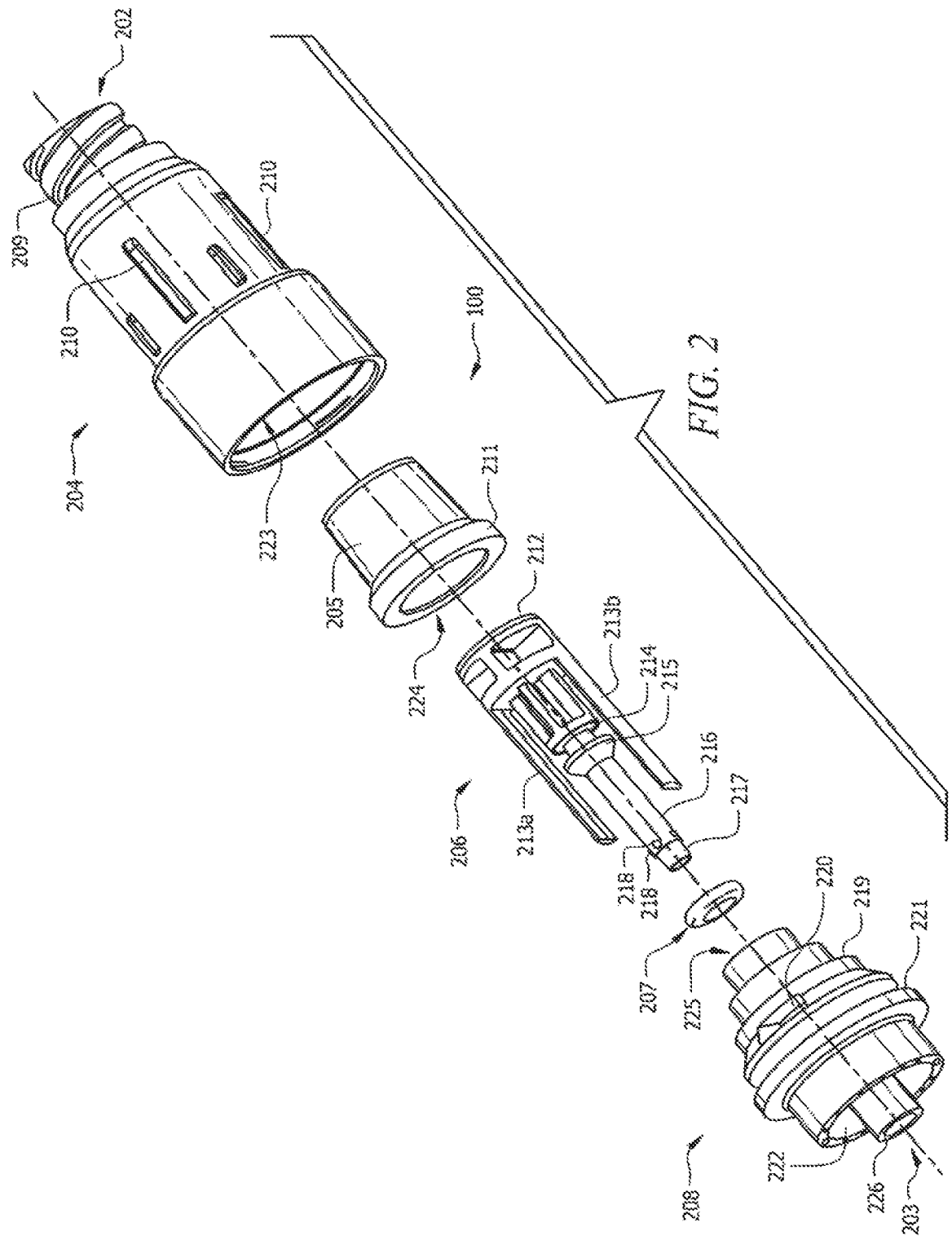

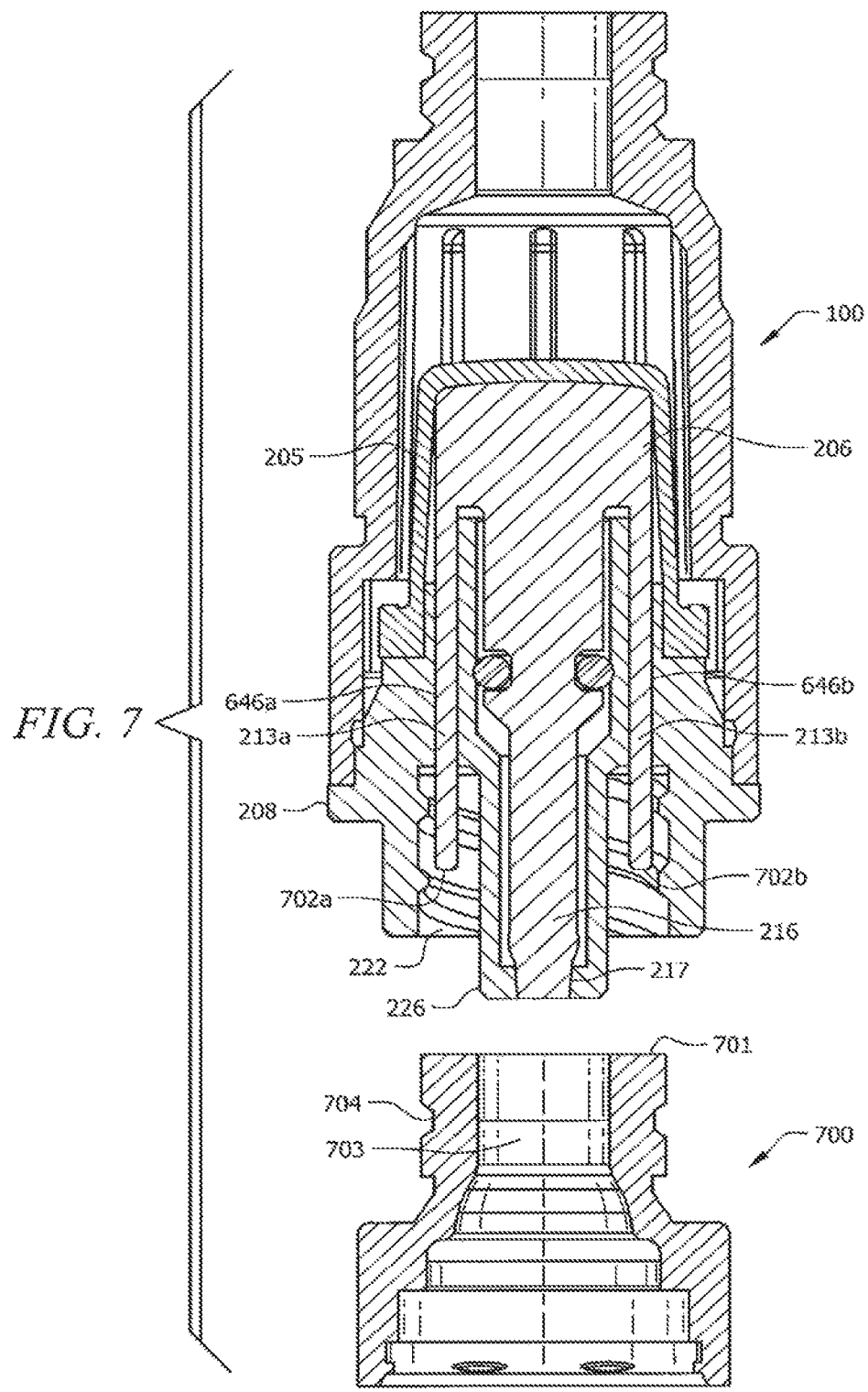

CLOSED MALE LUER DEVICE FOR USE WITH NEEDLELESS ACCESS DEVICES

CROSS REFERENCE TO RELATED APPLICATIONS

This application is a continuation of U.S. patent application Ser. No. 15/478,157, filed Apr. 3, 2017, entitled "CLOSED MALE LUER DEVICE FOR USE WITH NEEDLELESS ACCESS DEVICES," which is a continuation of U.S. patent application Ser. No. 14/172,756, filed Feb. 4, 2014, issued as U.S. Pat. No. 9,629,994, and entitled "CLOSED MALE LUER DEVICE FOR USE WITH NEEDLELESS ACCESS DEVICES," which is a continuation of U.S. patent application Ser. No. 13/455,090, filed Apr. 24, 2012, issued as U.S. Pat. No. 8,641,685, and entitled "CLOSED MALE LUER DEVICE FOR USE WITH NEEDLELESS ACCESS DEVICES," which is a continuation of U.S. patent application Ser. No. 12/418,809, filed Apr. 6, 2009, issued as U.S. Pat. No. 8,182,452, and entitled "CLOSED MALE LUER DEVICE FOR USE WITH NEEDLELESS ACCESS DEVICES," the disclosure of each of which is incorporated herein by reference in its entirety for all purposes.

BACKGROUND

The present invention relates to medical connectors used in fluid delivery applications, and more specifically to connectors that minimize fluid leakage during connection and disconnection.

Medical connections are widely used in fluid delivery systems such as those used in connection with intravenous fluid lines, blood access, hemodialysis, peritoneal dialysis, enteral feeding, drug vial access, etc. Many prior art aseptic medical connections have been designed to puncture an elastomeric diaphragm or septum, which has one side in contact with the fluid, with a sharpened hollow hypodermic needle. The use of such hypodermic needles has been gradually decreasing as a result of both safety and cost considerations associated with infectious disease acquired from needle sticks. These connectors have been replaced with luer activated connectors which don't require hypodermic needles, but instead use an activator such as a luer on the end of a syringe or IV line to create a fluid path though a valve in a connector. The removal of the connector causes the valve to close when the line is disconnected. Such a system is described in U.S. Pat. No. 5,569,235 to Ross et al.

Typical connectors and valves of this type, such as described by Ross, have many attributes that are not ideal in medical applications for delivery of fluids that could be harmful if contacted by the health care provider or the patient other than through the patient's intravenous ("IV") connection. Oncology drugs such as chemotherapy are examples of fluids that while beneficial to the patient as part of a treatment regimen could be extremely harmful to the health care provider if the chemotherapy drug were to come into contact with the skin of the health care provider or patient.

Traditional medical connectors require the health care provider to exercise great care on connection or disconnection due to the likelihood of the drug remaining inside the connector or dripping, particularly on disconnection when the connectors are primed with fluid. Some female connectors are designed to push fluid in the throat of the connector to the surface during disconnection. While this is desirable for aseptic connectors to provide a swabbable surface, it can result in fluid drips from the device on disconnection. Other connectors use a membrane with a septum that can also allow fluids to escape the connector.

What is needed is a connector for medical fluids that has standardized connections for use with existing medical connectors and also minimizes or eliminates drips on connection or disconnection.

Embodiments of the concepts described herein describe a medical connector which is formed by a body having an inlet port, an outlet port through a male luer portion of the body, and a fluid path between the inlet port and the at least one outlet ports. A retractable post extends through the fluid path in the male luer sealing a tip of the male luer thereby closing the fluid path when the connector in not activated. Barbs extending along the exterior of the male luer and connected to the retractable post, wherein when the connector is activated, the barbs force the retractable post away from the tip of the male luer thereby opening the fluid path through the medical connector. A retention member applies force to the post to force the post to seal the tip of the male luer when the medical connector is not activated.

In another embodiment of the concepts described herein a method for activating a medical connector is described. The medical connector includes a body having an inlet port and an outlet port the outlet port being part of a male luer. The connector further includes a post extending through a flow channel in the male luer and one or more barb arms connected to the post and adjacent to an outer surface of the male luer. The method includes inserting the male luer of the medical connector into a female luer of a secondary device, engaging the barb arms of the medical connector with a surface of the female luer, and retracting the post from the outlet port of the medical connector in response to the engagement of the barb arm with the female luer, wherein the retraction of the post from the outlet port opens a fluid path through the medical connector.

In another embodiment a closed male luer medical connector is described which includes a body formed by a top and a base, the body having an internal cavity and flow channels formed in walls of the internal cavity, the body further having an inlet port and an outlet port, the outlet port including a male luer, wherein the male luer defines a flow channel along its length. The connector also includes a body having a top in the internal cavity of the body; a post extending from the top and having a portion that extends the length of the flow channel, a tip of the post sized to seal the male luer thereby closing the flow channel when the post is fully extended into the male luer, the post further comprising one or more barb arms extending through vent holes in the body and adjacent to an external surface of the male luer, and an elastic cup, the elastic cup having a seating ring held in a fixed position by the body and a cup extending into the internal cavity and receiving the top of the post. Pressure applied to the barb arms in a direction parallel to the male luer and away from the outlet port results in the top of the body being forced up into the internal cavity and the post being drawn out of the outlet port, thereby unsealing the male luer, opening the flow channel through the medical connector. The elastic cup applies tension to the post body, the tension forcing the post back into the sealed position when the force on the barb arms is removed.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 2 is an exploded view of the embodiment of a male luer medical connector shown in FIG. 1;

FIG. 7 is a sectional view of the male luer medical connector from FIG. 1 illustrating the relationship between the male luer of the medical connector and a female luer connector and the fluid path through the connector;

DETAILED DESCRIPTION

Figure 1:
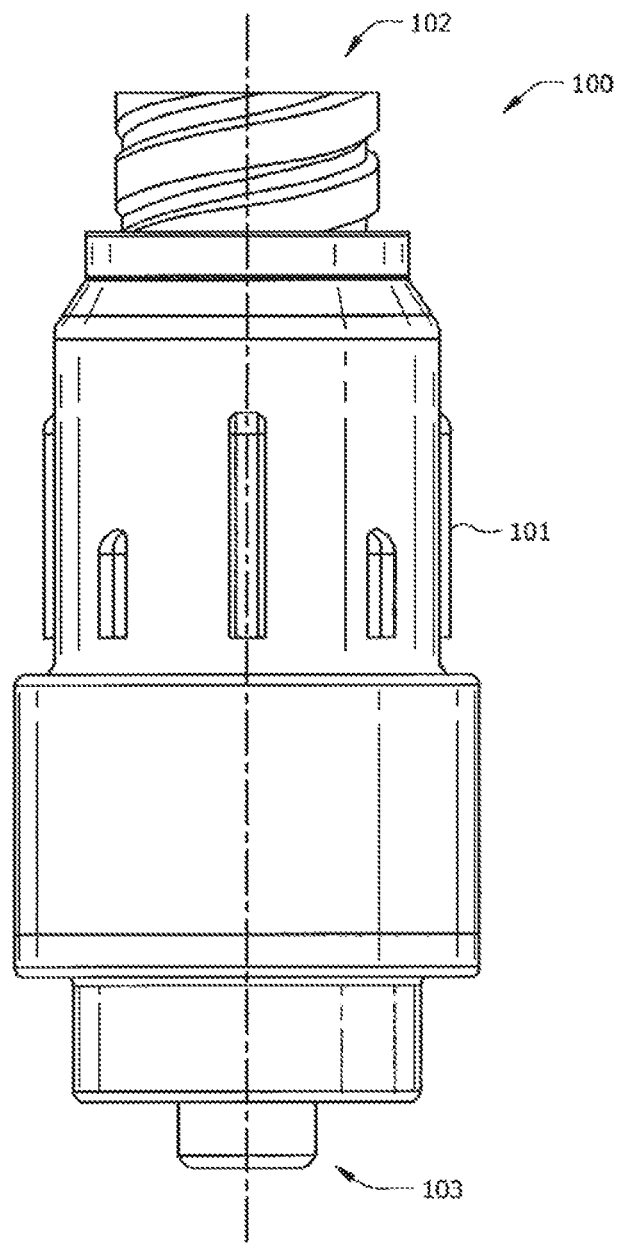
FIG. 1 is a side view of an embodiment of a male luer medical connector for fluid delivery according to the concepts described herein.

Referring now to FIG. 1, an embodiment of a medical connector 100 in accordance with the concepts described herein is shown. Medical connector 100 operates as a needleless access device and has a body 101 with a female access port 102 and a male lure 103. The male luer 103 is ISO compatible and compliant and interfaces with standard needless access devices. Medical connector 100 differs from access devices in that male luer 103 is closed, thereby preventing any fluid flow or leakage until activated by being inserted into a female luer. While connector 100 is shown with a threaded female luer at its distal end any type of inlet port could be used while remaining within the concepts described herein. Such inlet ports could include know connections for any type of fluid delivery sources or devices such as IV fluid bags, pumps or the like.

As with traditional needleless medical connectors, male luer 103 of medical connector 100 is inserted into the female luer of another needleless access device to create a fluid path between a fluid delivery mechanism and a patient. In order to avoid drips and leakage of medical fluids that may be harmful to health care providers or patients, medical connector 100 is designed to minimize or eliminate fluid drips or leakage upon connection of medical connector 100 with another access device, or particularly upon disconnection from another access device with both devices are primed with fluid.

Referring now to FIG. 2, the embodiment of the medical connector 100 shown in FIG. 1 is shown in an exploded view. Embodiments of the components that form medical connector 100 shown. The body of medical connector 100 includes top 204 having an inlet port 202 and a base 208, which includes outlet port 203. The medical connector also includes an elastic cup 205 formed from an elastic deformable material, a barb 206, and a sealing ring 207.

Top 204 can form a majority of the body of medical connector 100. Top 204 includes threaded female luer 209 which connects to the male luer of any other compatible device. Female luer 209 can be threaded to maintain the connection between devices. While connector 209 is shown as having a threaded female luer type connector, any type of inlet port could be used, such as a bond pocket or other connector, while remaining within the scope of the concepts described herein. Top 100 can also include ridges 210 along the outer surface of top 204. Ridges 204 provide for enhanced gripping surfaces when twisting forces are applied to medical connector 100 during connection and disconnection with other devices. Top 204 also includes cavity 223 which holds elastic cup 205 and barb 206 as will be described.

Elastic cup 205 is formed from an elastic deformable material allowing it to stretch and then return to its original state. Elastic cup 205 fits into cavity 223 of top 204 and includes cup cavity 224 for receiving top 212 of barb 206. Seating ring 211 is used to hold elastic cup 205 between top 204 and base 208.

Figure 5:
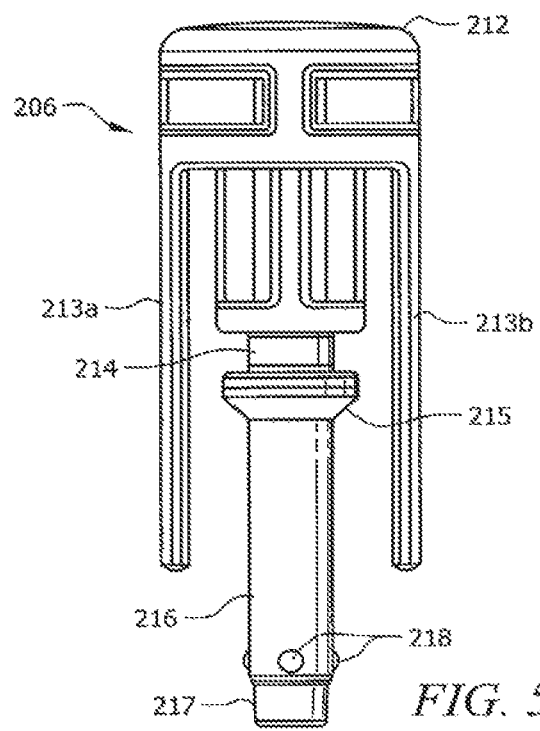
FIG. 5 is a side view of an embodiment of the barb of the male luer medical connector shown in FIG. 2.

Barb 206, which may also be referred to as a post body, is used to open and close the fluid path through medical connector 100 as will be described. Additional reference is made to FIG. 5 in the description of barb 206. Barb 206 includes top 212 which fits into elastic cup 205. Barb arms 213a and 213b extend downward from the radial edge of top 212 and engage a surface of an activating connector. Sealing ring seat 214 receives sealing ring 207, which is held in place by flange 215. Post 216 extend downward from the center of top 212 parallel to barb arms 213a and 213b. Post 216 includes tapered end 217 which mates with the end outlet port 203 in base 208. Bumps 218 arranged around the circumference of post 216 keep post 216 centered in base 208 and provide space for fluid to flow around post 216 of barb 206.

Base 208 mates with top 204 thereby holding elastic cup 205, barb 206 and sealing ring 207 in cavity 223 of top 204. Top 204 is secured to the base 208 using conventional means, such as solvent bonding, ultrasonics, spin welding, etc. Base 208 includes channel 225 which receives post 216 of barb 206.

Figure 3A:
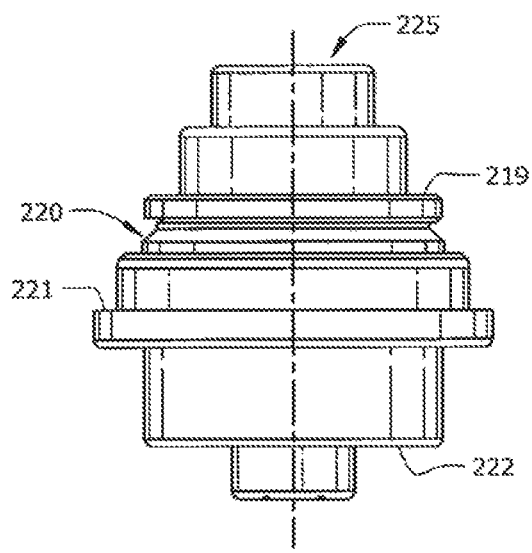
FIGS. 3A and 3B are side views of an embodiment of the base of the male luer medical connector shown in FIG. 2.
Figure 3B:
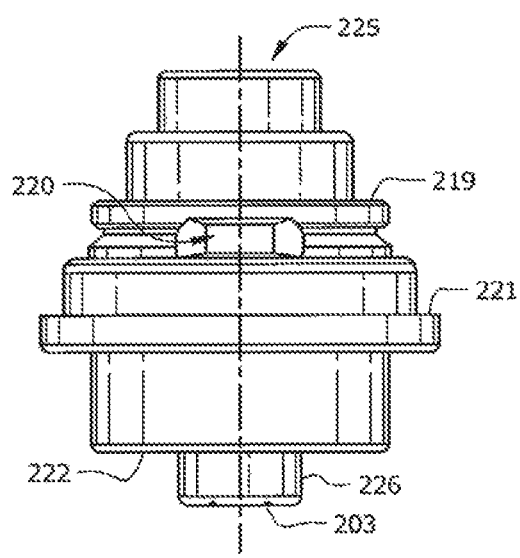

Referring additionally to FIGS. 3A and 3B which show side views of an embodiment of base 208 from FIG. 2, base 208 will be described in greater detail. Base 208 includes channel 225 which receives post 216 of barb 206. Sealing ring seat 219 engages the bottom surface of seating ring 211 to hold elastic cup 205 in place when medical connector 100 is assembled. Seating surface 221 mates with a corresponding surface (not shown) in top 204 to seal medical connector 100 except for the proscribed fluid path. Flow channels 220 allow for fluid flow through the base and into outlet port 203. While two channels are shown in base 208, any number of channels, including one or three or more, can be used without departing from the scope of the concepts described herein. Base 208 also includes male luer 226 and threaded connector 222.

Figure 3C:
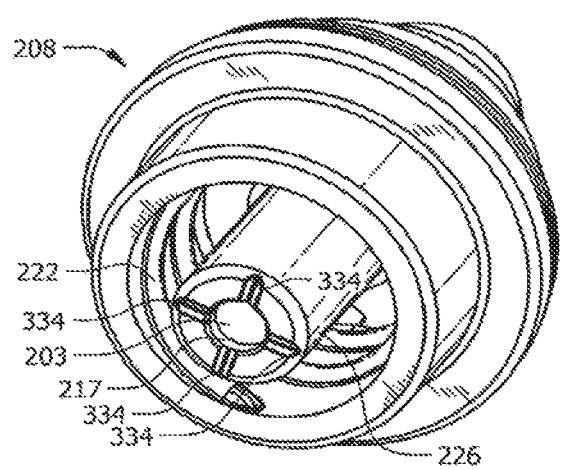
FIG. 3C is a perspective view showing the outlet port of an embodiment of the base of the male luer connector shown in FIG. 2.

FIG. 3C shows a perspective view of an embodiment of base 208 illustrating the outlet port end of base 208. As described, male luer 226 extends down through threaded connector 222 and includes the outlet port 203 of the fluid path though the connector. Channels 334 are formed in the end of male luer 226 to aid in the suction characteristics and fluid retraction of the connector upon disconnection as will be described in greater detail below. Channels 334 assist in the retraction of fluid upon disconnect by directing fluid into tapered end 217 of outlet port 203 throughout the disconnection process.

Figure 4:
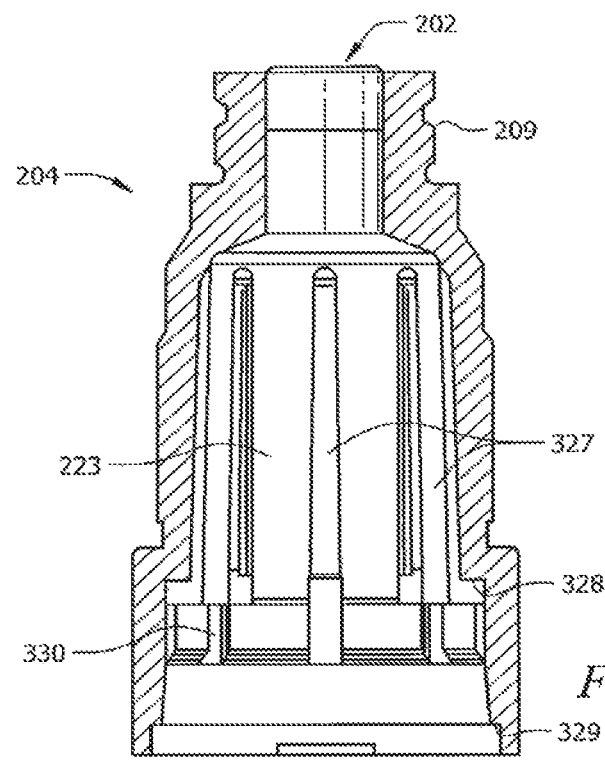
FIG. 4 is a sectional view of an embodiment of the top of the male luer medical connector show in FIG. 2.

Referring now to FIG. 4, an embodiment of top 204 is shown in a sectional view. As described, top 204 includes an inlet port 202 for receiving the male luer of another compatible device. As described with respect to FIG. 2, cavity 223 receives elastic cup and barb, and as will be discussed, provides room for barb 206 from FIG. 2 to move longitudinally within cavity 223. Cavity 223 also includes flow channels 327 molded into the internal walls of cavity 223. While the flow channels 223 are shown symmetrically spaced around the internal wall of cavity 223, any number, size, spacing or configuration of flow channels could be used without departing from the scope of the concepts described herein.

The internal surface of cavity 223 of top 204 also includes elastic cup seat 328 which works cooperatively with seating ring seat 219 of base 208, shown in FIGS. 3A and 3B to hold seating ring 211 of elastic cup 205 in place when the medical connector is assembled. Base seat 329 mates with seat 221 from FIGS. 3A and 3B to assemble and seal top 204 to base 208.

Figure 6A:
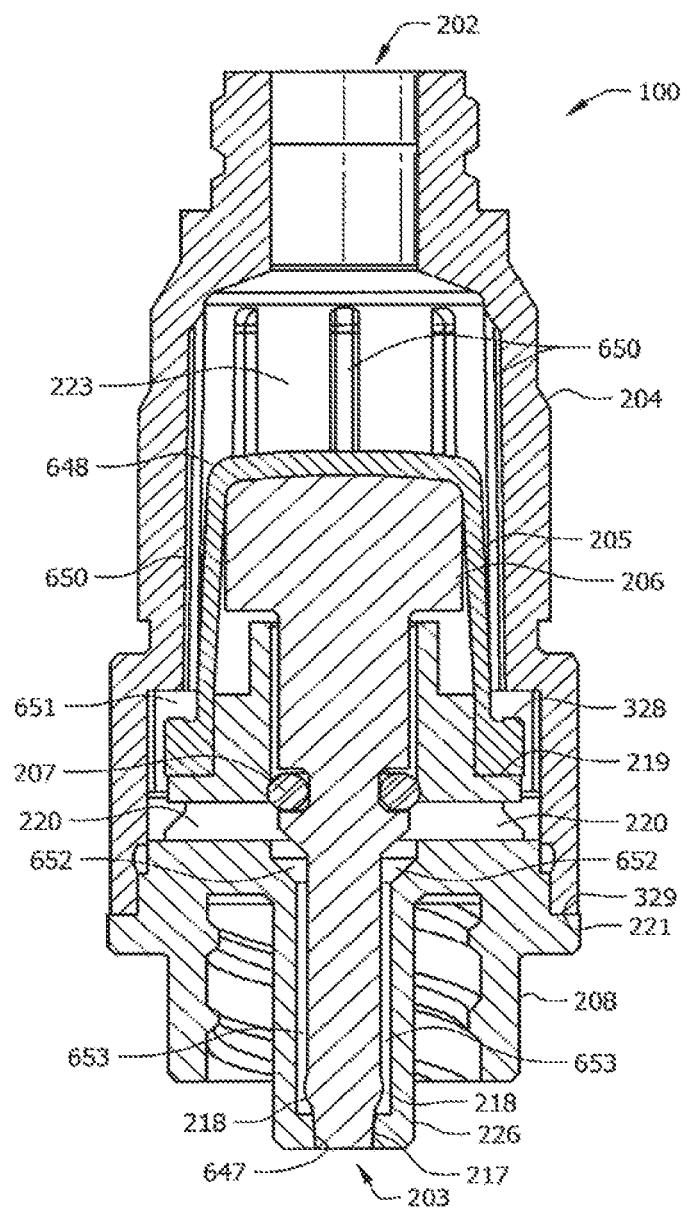
FIG. 6A is a section view of the male luer medical connector from FIG. 1.
Figure 6B:
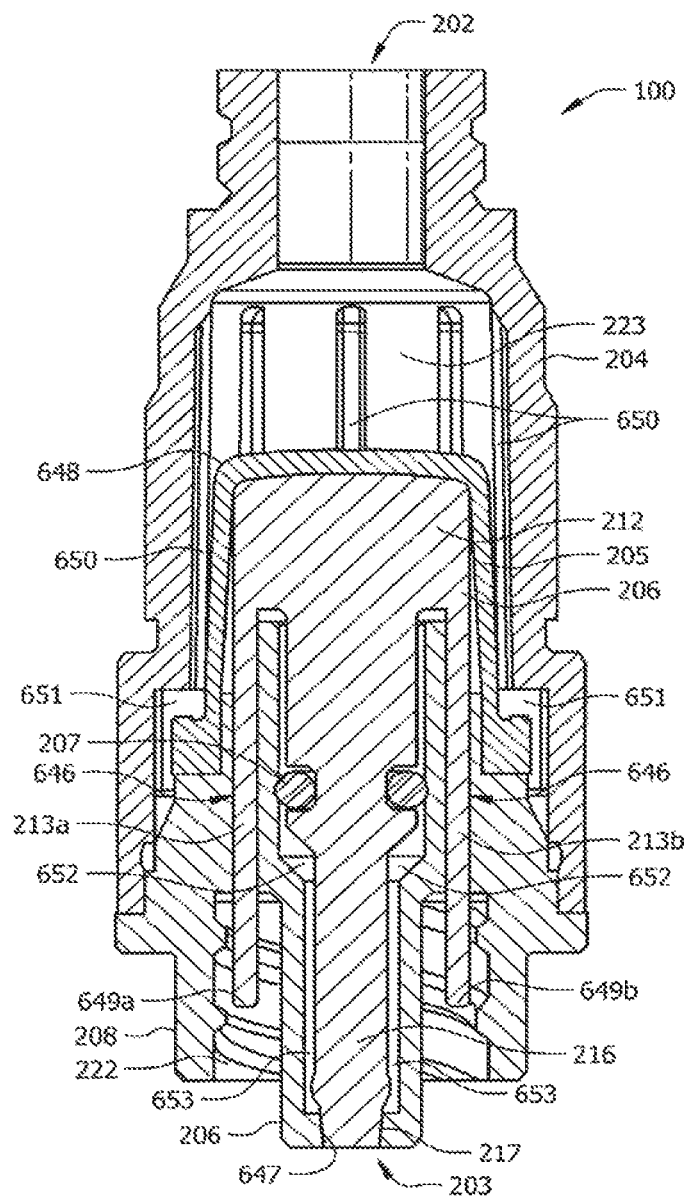
FIG. 6B is a section view of the male luer medical connector shown in FIG. 1 rotated 90° along its longitudinal axis from the view in FIG. 6A.

Referring now to FIGS. 6A and 6B, an embodiment of a medical connector 100 is shown assembled in section view. FIG. 6B is a sectional view of the medical connector shown in FIG. 6A rotated 90° around its longitudinal axis. As has been described, a preferred embodiment of medical connector 100 is formed by the assembly of top 204 to base 208. Within the cavity 223 formed by top 204 and base 208, barb 206 and elastic cup 205 are housed. Sealing ring 207 fits into sealing ring seat 214.

Top fluid path 650 communicates with junction fluid path 651 and base fluid path 652, using channel 220, before arriving at post fluid path 653 which is in communication with outlet port 203 in male luer portion 226 of connector 100. Unlike other similar medical connectors in which the fluid path flows directly from an inlet port through a channel inside a post and out the end of the outlet port in a male luer, fluid paths 650, 651, 652, through 653 channel flow around elastic cup 205, through channel 220 in base 208 and around post 216 of barb 206. This fluid path allows for the sealing of male luer 226 using tapered end 217 of post 216.

Top 212 of barb 206 fits into the cavity created by elastic cup 205. A ridge, or seating surface 328 formed in the inner wall of top 204 between the flow channels mates with the top surface of seating ring 211, while the bottom surface of seating ring 211 mates with seating ring seat 219 in base 208. When assembled seating ring 211 of elastic cup 205 is held firmly in place between top 204 and base 208. Cup portion 648 of elastic cup 205 may deform or stretch up into cavity 223 of top 204.

Cup portion 648 also acts to place tension on barb 206, acting to force barb 206 toward base 208 which acts to force tapered end of post 216 into tapered channel 647 of male luer 226. When tapered end 217 is pressed into tapered channel 647, male luer 226 is blocked, thereby preventing fluid flow through medical connector 100.

Referring specifically to FIG. 6B, it can be seen that the embodiment of base 208 shown includes vent holes 646a and 646b. Barb arms 213a and 213b extend downward through vent holes 646a and 646b and protrude into the cavity forming threaded connector 222. Sealing ring 207 prevents fluid in fluid path 652 from flowing up and into vents 646a and 646b. As will be discussed below, barb arms 213a and 213b can be engaged by a surface of a male luer to push barb 206 and cup 648 up into cavity 223 extracting tapered end 217 of post 216 from tapered channel 647 of male luer 226 and thereby opening the flow path through medical connector 100.

Referring now to FIG. 7, a sectional view of the embodiment of medical connector 100 shown in FIG. 1 is described in relation to a complimentary connector 700. Medical connector 100, in accordance with the concepts described herein, includes a closed male luer that prevents fluid flow until activated by insertion into a complimentary female luer connector. As described, elastic cup 205 places a positive pressure on barb 206, thereby keeping tapered end 217 of post 216 firmly seated in male luer 226 of base 208. Barb arms 213a and 213b extend through vent holes 646a and 646b, respectfully, and into the cavity form by connector 222.

Female connector 700 includes female luer 703 which includes threaded connector 704 and top surface 701. As can be seen, when female connector 700 is threaded onto medical connector 100 such that male luer 226 engages with female luer 703, top surface 701 of female connector 700 will engage the bottom surfaces 702a and 702b of barb arms 213a and 213b, respectively. As female connector 700 continues to be threaded into medical connector 100, the engagement of top surface 701 with barb arms 213a and 213b will force barb 206 up into medical connector 100, elongating elastic cup 205.

Figure 8A:
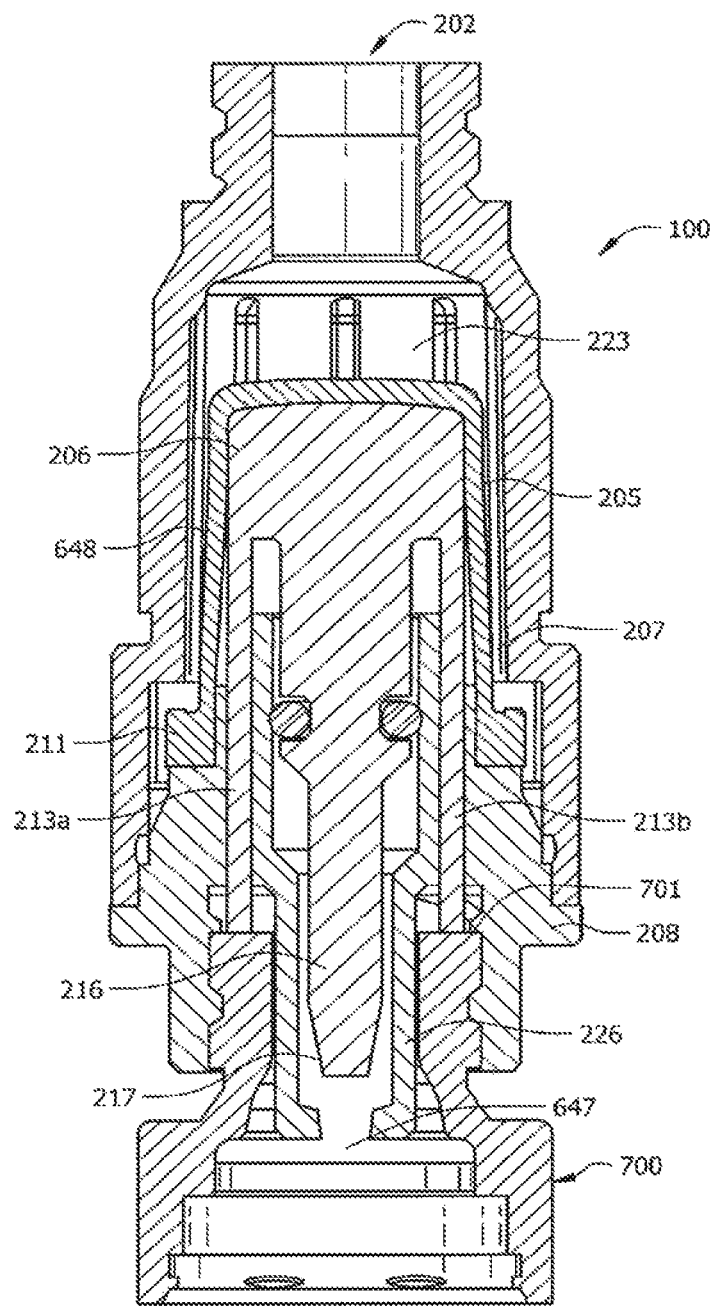
FIGS. 8A and 8B are sectional views of the male luer medical connector from FIG. 1 illustrating the barb engaging the female luer connector and opening the fluid path through the connector.
Figure 8B:
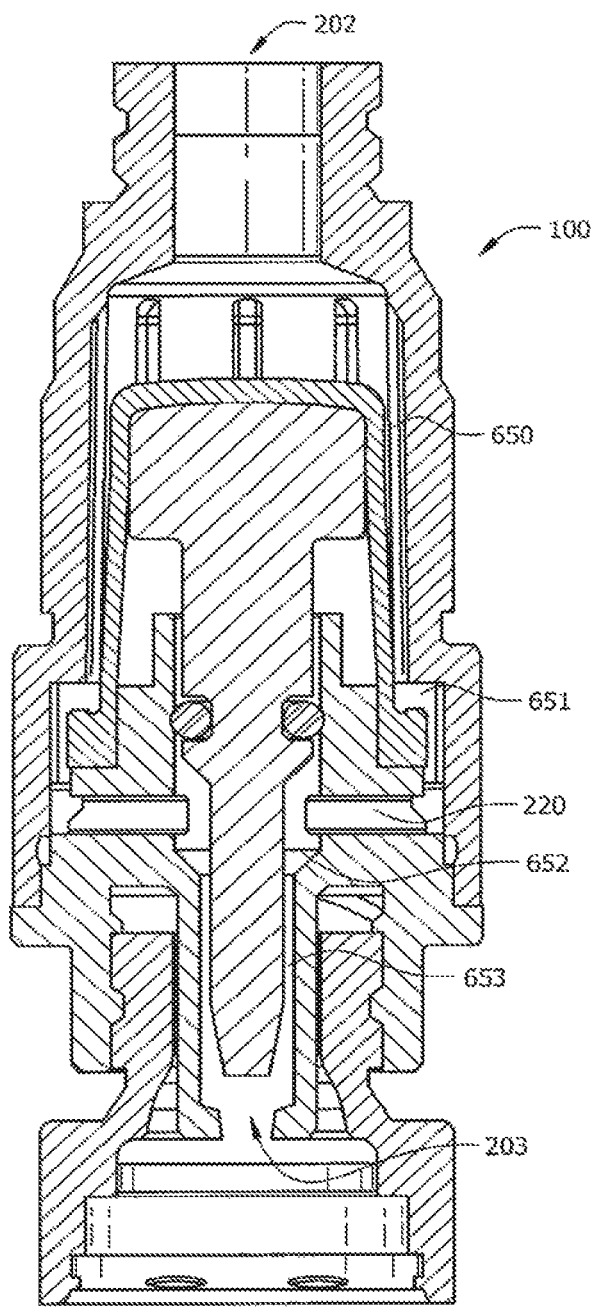

Referring now to FIGS. 8A and 8B, sectional views of the embodiment of medical connector 100 shown in FIG. 1 are shown activated by the complimentary connector 700 of FIG. 7. The term activate or activated, as used herein has the same meaning a connected or engaged, while the term deactivated has the same meaning as disconnected or disengaged. As described with reference to FIG. 7, when male luer 226 is activated by female connector 700 by inserting male luer into female connector 700, top surface 701 of female connector 700 engages barb arms 213a and 213b of barb 206. As barb 206 is pushed upward into cavity 223 of top 204, seating ring is held in place between the opposing surfaces of top 204 and base 208 while cup 648 of elastic cup 205 stretches to accommodate the rise of barb 206. The rise of barb 206 results in the rise of post 216 causing tapered end 217 to disengage from tapered channel 647 creating an open fluid path from medical connector inlet port through outlet port 203 and into female connector 700. The deformation of elastic cup 205 provides tension on barb 206 so that when female connector 700 is removed from male luer 226, the force supplied by elastic cup 205 causes barb 206 to return to the closed position with tapered end of post 216 again sealing tapered channel 647 of male luer 226.

The fluid path when medical connector 100 is engaged with female connector 700 can be seen clearly in FIG. 8B with reference to elements in FIG. 8A. In the open fluid path configuration, fluid enters through inlet port 202 and flows into cavity 223 of top 204. Fluid continues in top fluid path 650 which flows through flow channels 327 as described with respect to FIG. 4. Fluid continues through junction fluid path along flow channels 330 also described with respect to FIG. 4 and then into channels 220 through base 208 into fluid path 652. From channels 220 and fluid path 652, the fluid continues through post fluid path 653 which extends the along the length of male luer 226 between the inner surface of the male luer and post 216 of barb 206. Fluid then exits out of outlet port 203 through tapered channel 647 and flows into female connector 700.

As can be seen from FIGS. 8A and 8B, activation or connection of medical connector 100 to another device causes post 216 to push elastic cup 205 up into cavity 223 thereby decreasing the volume of cavity 223. Upon deactivation or disconnection, the opposite occurs, cup 205 returns to its original state increasing the volume of cavity 223. This increase in the volume of cavity 223 has advantageous effects on the operation of medical connector 100. Namely, the increase in the fluid volume held by medical connector 100 at disconnection provides a suction force, or negative displacement force on the fluid on male luer 226, thereby drawing the fluid out of male luer 226 and into medical connector 100. Channels 334 in the end of male luer 226, as shown in FIG. 3C provide a path for the suction force and fluid retraction into outlet port 203 as the connector is being disengaged. Without channels 334, the tip of male luer 226 could be closed by the receiving device until the moment of complete separation possibly preventing the fluid retraction before that moment.

This suction acts to clean any fluid in the vicinity male luer opening, preventing leaks or drops escaping from the medical connector at disconnection, which is very important when working with blood or potentially harmful medicines such as those used in chemotherapy. Traditional connectors have required medical professionals to clamp a line in the system to prevent leakage upon disconnection. Such clamping, while potentially beneficial in that it would prevent the suction created by the increase in fluid volume at disconnection from drawing fluid from the source line, is not necessary with embodiments of connectors as described herein to prevent leakage or dripping.

Figure 9:
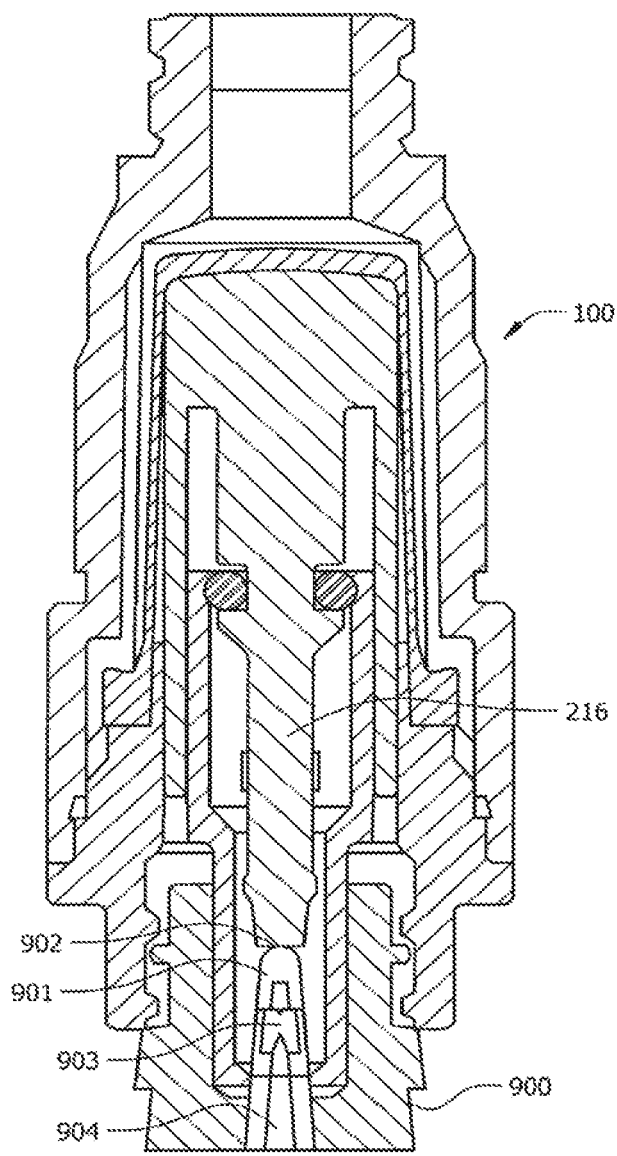
FIG. 9 is a sectional view of the medical connector from FIG. 1 illustrating an alternative mechanism for opening the fluid path through the connector.

Referring now to FIG. 9, and alternate embodiment of a female connector for activating a closed male luer medical connector 100 according to the concepts describe herein is shown. While FIGS. 8A and 8B demonstrate a closed male luer medical connector according to the concepts described herein being opened using the bard arms of barb 206 from FIG. 2, female connector 900 may also include a spike to cause activation of the closed male luer. Spike 901 engages bottom surface 902 of post 216 moving post 216 away from tapered channel 647. Spike 901 includes inlet ports 903 which allow fluid from medical connector to flow into channel 904 in spike 901.

While medical connector 100 shown in FIGS. 2-9 uses the elastic nature of elastic cup 205 to force barb 206 into a closed position when not engaged with a female connector, other mechanisms may be used to accomplish the same purpose without departing from the concepts described herein. FIGS. 10A-D illustrate embodiments of other medical connectors that use other mechanisms to force the post into a sealing position.

Figure 10A:
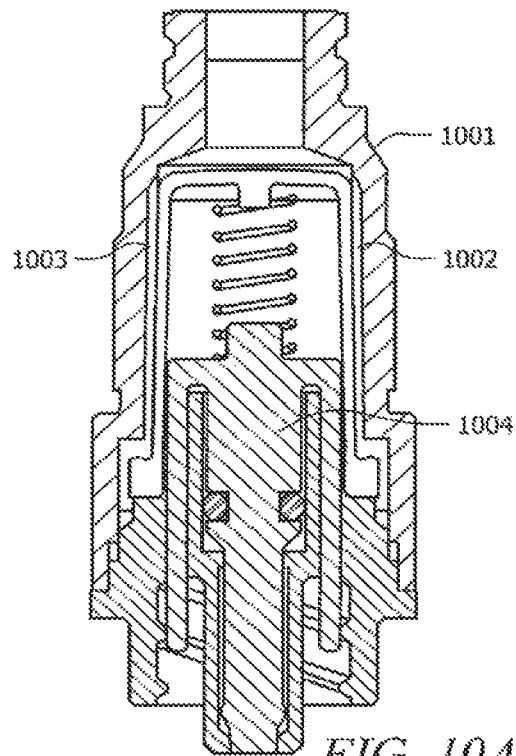
FIGS. 10A-10D are alternate embodiments of a male luer medical connector according to the concepts described herein.
Figure 10B:
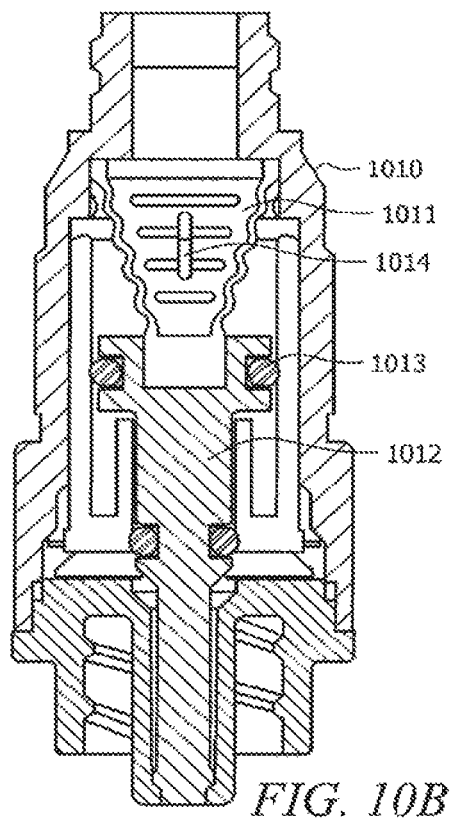

FIG. 10A shows an embodiment of a medical connector 1001 that replaces the elastic cup with a rigid cup 1002 and uses spring 1003 to provide the force against post 1004. Connector 1001, by using a rigid cup will providing a constant priming volume. FIG. 10B shows a connector 1010 that uses an inverted bellows valve 1011 to provide the elastic force on post 1012. Slits 1014 in inverted bellows valve 1011 allow fluid to pass through and in to the fluid path. Additional seal 1013 is required to prevent fluid from flowing into the vent holes in the base.

Figure 10C:
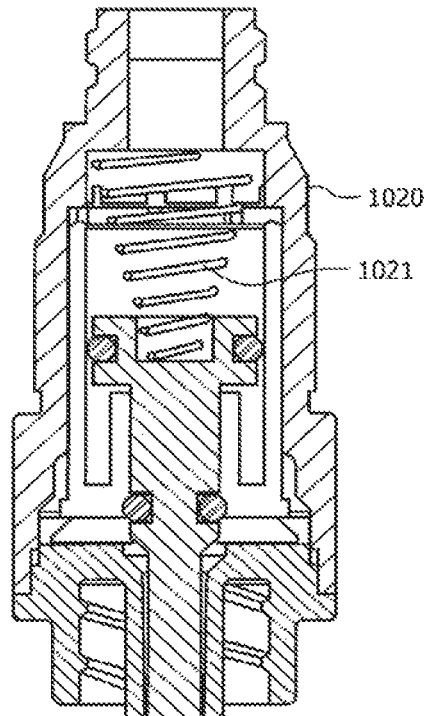
Figure 10D:
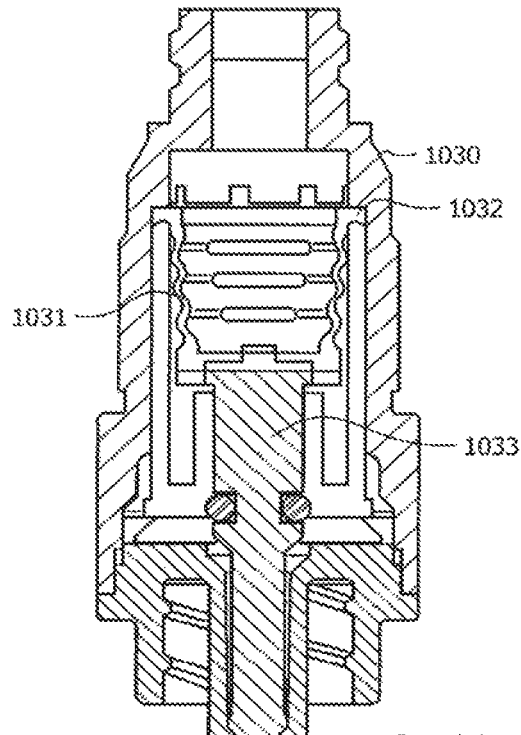

FIG. 10C shows a embodiment of a medical connector 1020 substantially as described with respect to FIG. 10B except that the inverted bellows valve is replaced with an inverted helix spring 1021. FIG. 10D shows an alternate embodiment of a bellows valve. Medical connector 1030 uses a bellows valve 1031 as was described with respect to FIG. 10B to provide the elastic force on post 1033. However, instead of using slits and passing the fluid through the bellows valve, connector 1030 includes a seal 1032 which directs the fluid over and around bellows valve 1031 and into the fluid path through connector 1030.

The top, base and barb elements are preferably formed from polycarbonate plastic but could be formed from any number of materials appropriate for medical connectors. The elastic cup and the bellows described herein are preferably made from medical grade silicon, but can be made from any material that has the characteristics described with respect to those elements. The female connector used with a medical connector according to the concepts described herein may be any type of female connector such as those having a valve plug arrangement, bellows type plugs, devices with septums, or other configurations designed to accept standardized male luer connectors.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A medical connector comprising:
 a body comprising a cavity, a first port, and a second port through a male luer portion of the body;
 a bellows valve comprising a seating ring and a cup portion, the seating ring coupled to the body with the cup portion positioned in the cavity to separate the cavity into a first volume and a second volume, wherein a fluid path extends between the first port, the first volume, and the second port; and a post extending into the male luer, wherein, when the connector is in a closed configuration, the fluid path through the second port is sealingly closed by the post, and when the connector is in an open configuration, the post is moved away from the second port to open the fluid path and urge the cup portion toward the first port to decrease the first volume in the cavity.

2. The medical connector of claim 1, wherein the post is positioned between the bellows valve and the second port such that the post is urged toward the second port by the bellows valve.

3. The medical connector of claim 1, comprising a barb arm extending from the post and along an outer surface of the male luer, wherein, when the connector is activated, the barb arm is engaged by a secondary device to urge the barb arm and the post toward the first port.

4. The medical connector of claim 1, wherein the body comprises a vent passage between the second volume and an outer surface of the connector.

5. The medical connector of claim 1, wherein a seal ring is positioned between the post and the body such that the first volume is fluidly isolated from the second volume.

6. The medical connector of claim 1, wherein a portion of the fluid path, between the first port and the second port, extends between an outer surface of the post and an inner surface of the body.

7. The medical connector of claim 1, wherein the post comprises an outer surface having a protrusion configured, such that the outer surface of the post is separated from an inner surface of the male luer portion.

8. The medical connector of claim 1, wherein the male luer portion comprises an outer channel extending along an outer surface of the male luer portion.

9. The medical connector of claim 8, wherein the outer channel extends from the second port to a periphery of a tip of the male luer.

10. The medical connector of claim 1, wherein the bellows valve comprises a slit extending therethrough, and wherein a portion of the fluid path extends through the slit.

11. The medical connector of claim 1, wherein a first portion of the post extends into the male luer, and a second portion of the post extends into the cup portion.

12. A method for providing a negative displacement medical connector, the method comprising:

providing body comprising a fluid path extending between a first port, a cavity, and a second port, the second port forming a male luer portion of the body;

providing a bellows valve having a seating ring and a cup portion, the seating ring coupled to the body with the cup portion positioned in the cavity to separate the cavity into a first volume and a second volume;

positioning a post in the male luer with the cup portion engaged against a portion of the post to urge the post toward the second port to seal the fluid path through the second port when the connector is in a closed configuration; and moving the post away from the second port to open the fluid path and urge the cup portion further toward the first port to decrease the first volume in the cavity when the connector is in an open configuration.

13. The method of claim 12, wherein moving the post away from the second port comprises engaging a portion of the post with a secondary device comprising a female luer portion.

14. The method of claim 13, comprising disengaging the secondary device to permit the post to seal the fluid path through the second port while increasing the first volume, thereby drawing a fluid into the medical connector through the second port.

15. The method of claim 14, wherein drawing a fluid into the medical connector through the second port comprises drawing the fluid through an outer channel extending along on an outer surface of the male luer portion.

16. The method of claim 12, wherein moving the post comprises engaging a barb arm, extending from the post and along an outer surface of the male luer, with a secondary device comprising a female luer portion.

17. The method of claim 12, wherein moving the post toward the first port comprises urging the post toward the first port.

18. The method of claim 12, wherein urging the cup portion toward the first port comprises permitting air to move through a vent passage between the second volume and an outer surface of the connector.

19. The method of claim 12, wherein forming the second volume and the first volume of the cavity comprises positioning a seal ring between the post and the body such that the first volume is fluidly isolated from the second volume.

20. The method of claim 12, wherein moving the post away from the second port to open the fluid path comprises opening a slit through the bellows valve.

* * * * *